United States Patent [19]

Kuroda et al.

[11] Patent Number: 4,950,572
[45] Date of Patent: Aug. 21, 1990

[54] PHOTOCONDUCTOR FOR ELECTROPHOTOGRAPHY WITH THIENYL GROUP CONTAINING CHARGE TRANSPORT MATERIAL

[75] Inventors: Masami Kuroda; Youichi Nakamura; Noboru Furusho, all of Kawasaki, Japan

[73] Assignee: Fuji Electric Co., Ltd., Kanagawa, Japan

[21] Appl. No.: 324,425

[22] Filed: Mar. 16, 1989

[30] Foreign Application Priority Data

Mar. 17, 1988 [JP] Japan .................. 63-64615

[51] Int. Cl.⁵ .................. G03G 5/06; G03G 5/12
[52] U.S. Cl. .................. 430/59; 430/96
[58] Field of Search .................. 430/59, 96

[56] References Cited

U.S. PATENT DOCUMENTS

| | | | |
|---|---|---|---|
| 4,150,987 | 8/1979 | Anderson et al. | 430/59 |
| 4,353,971 | 7/1982 | Chang et al. | 430/58 |
| 4,385,106 | 5/1983 | Sakai | 430/59 |
| 4,448,868 | 5/1984 | Suzuki et al. | 430/58 |
| 4,565,761 | 3/1986 | Katagiri et al. | 430/83 |
| 4,629,670 | 1/1986 | Katagiri et al. | 430/58 |
| 4,673,630 | 5/1987 | Katagiri et al. | 430/72 |
| 4,677,045 | 11/1987 | Champ et al. | |
| 4,839,252 | 4/1989 | Murata et al. | 430/59 |
| 4,861,691 | 8/1989 | Kuroda et al. | 430/59 |
| 4,861,692 | 1/1989 | Kuroda et al. | 430/59 |

FOREIGN PATENT DOCUMENTS

| | | | |
|---|---|---|---|
| 59-182456 | 10/1984 | Japan | 430/59 |
| 59-182457 | 10/1984 | Japan | 430/59 |

*Primary Examiner*—Roland E. Martin
*Attorney, Agent, or Firm*—Spencer & Frank

[57] ABSTRACT

The photoconductor for electrophotography comprises a novel hydrazone compound as a charge transporting substance. The hydrazone compound is represented by the following general formula:

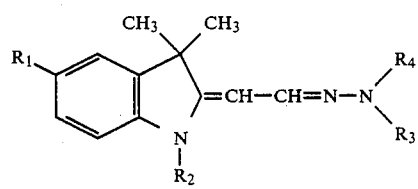

wherein, $R_1$ stands for a hydrogen atom, a halogen atom, a hydroxy group, an alkoxy group or a nitro group, each of $R_2$, $R_3$ and $R_4$ stands for an aryl group, an alkyl group, an aralkyl group, each of which may have a substituent(s), and at least one of $R_2$, $R_3$ and $R_4$ stands for a thenyl group which may have a substituent.

9 Claims, 1 Drawing Sheet

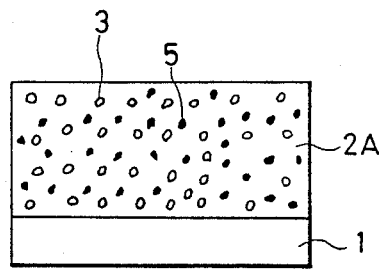
F I G. 1
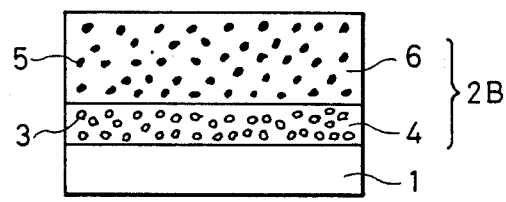
F I G. 2
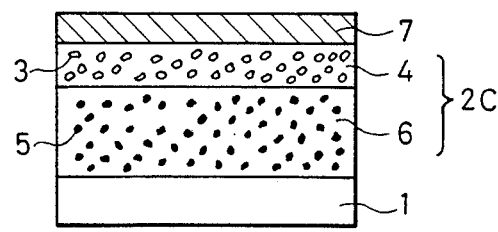
F I G. 3

PHOTOCONDUCTOR FOR ELECTROPHOTOGRAPHY WITH THIENYL GROUP CONTAINING CHARGE TRANSPORT MATERIAL

BACKGROUND OF THE INVENTION

1. FIELD OF THE INVENTION

The present invention relates to photoconductors for electrophotography, and particularly to a photoconductor for electrophotography which contains a novel hydrazone compound in the photosensitive layer thereof formed on an electroconductive substrate.

2. DESCRIPTION OF THE PRIOR ART

Photosensitive materials which have heretofore been used in photoconductors for electrophotography include inorganic photoconductive substances such as selenium and selenium alloys, dispersions of inorganic photoconductive substances such as zinc oxide and cadmium sulfide in resin binders, organic polymeric photoconductive substances such as poly-N-vinylcarbazole and polyvinylanthracene, organic photoconductive substances such as phthalocyanine compounds and bisazo compounds, and dispersions of such organic polymeric photoconductive substances in resin binders.

Photoconductors are required to have a function of maintaining a surface electric charge in the dark, a function of generating an electric charge upon receiving light, and a function of transporting an electric charge upon receiving light. They are classified into two types of photoconductors, namely so-called monolayer type photoconductors, and so-called laminate type photoconductors. The former comprises a single layer having all of the above-mentioned three functions, and the latter comprises functionally distinguishable laminated layers, one of which contributes mainly to the generation of electric charge, and another of which contributes to the retention of surface electric charge in the dark and the transportation of electric charge upon receiving light. In an electrophotographic method using a photoconductor of the kind as mentioned above, for example, the Carlson's system is applied to image formation. The image formation according to this system comprises steps of subjecting a photoconductor in the dark to corona discharge to charge the photoconductor, illuminating the surface of the charged photoconductor with imagewise light based on a manuscript or copy bearing, e.g., letters and/or pictures to form a latent electrostatic image, developing the formed latent electrostatic image with a toner, and transferring the developed toner image to a support such as a paper sheet to fix the toner image on the support. After the toner image transfer, the photoconductor is subjected to the steps of removal of the electric charge, removal of the remaining toner (cleaning), neutralizaiton of the residual charge with light (erasion), and so on to be ready for reuse.

Photosensitive members for electrophotography in which use is made of an organic material have recently been put into practical use by virtue of the advantageous features of the organic materials such as flexibility, thermal stability, and/or a film forming capacity. They include a photoconductor comprising poly-N-vinylcarbazole and 2,4,7-trinitrofluoren-9-on (disclosed in U.S. Pat. No. 3,484,237), a photoconductor using an organic pigment as the main component (disclosed in Japanese Patent LaidOpen No. 37,543/1972), and a photoconductor using as a main component a eutectic complex composed of a dye and a resin (disclosed in Japanese Patent Laid-Open No. 10,785/1972). A number of novel hydrazone compounds have also been put into practical use for photoconductors.

Although organic materials have a number of advantageous features mentioned above with which inorganic materials are not endowed, however, the fact is that there have been obtained no organic materials fully satisfying all the characteristics required of a material to be used in photoconductors for electrophotography at the present. Particular problems involved in organic materials have been concerned with photosensitivity and characteristics in continuous repeated use.

SUMMARY OF THE INVENTION

An object of the present invention is to provide a photoconductor for electrophotography to be used in copying apparatuses and printers which photoconductor has a high photosensitivity and excellent characteristics in repeated use, through the use, in the photosensitive layer, of a novel organic materials not used to date as a charge transporting substance.

In the first aspect of the present invention, a photoconductor for electrophotography comprises:

a substrate; and a photosensitive layer formed on the substrate and including at least one hydrazone compound represented by the following general formula (I) as a charge transporting substance:

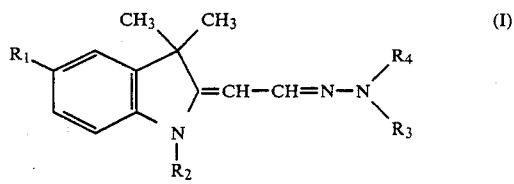

wherein, $R_1$ stands for a hydrogen atom, a halogen atom, a hydroxy group, an alkoxy group or a nitro group, each of $R_2$, $R_3$ and $R_4$ stands for an aryl group, an alkyl group, an aralkyl group, or alkenyl group, each of which may have a substituent(s), and at least one of $R_2$, $R_3$ and $R_4$ stands for a thenyl group which may have a substituent(s).

Here, the photosensitive layer may comprise a layer including a dispersion of a charge generating substance and a charge transporting substance selected from hydrazone compounds represented by the general formula (I) in a binder resin.

The photosensitive layer may comprise a laminate of a charge transporting layer including a charge transporting substance selected from hydrazone compounds represented by the general formula (I) and a charge generating layer.

In the second aspect of the present invention, a photoconductor for electrophotography comprises:

a substrate; and a photosensitive layer formed on the substrate and including at least one hydrazone compound represented by the following general formula (II) as a charge transporting substance:

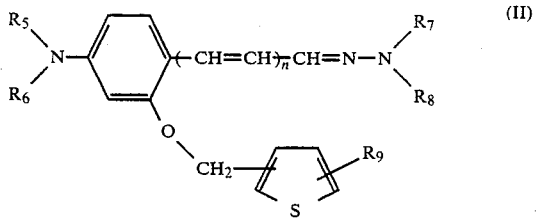

wherein, each of $R_5$, $R_6$, $R_7$ and $R_8$ stands for an alkyl group, an alkenyl group, an aryl group, an aralkyl group, each of which may have a substituent(s), $R_9$ stands for a hydrogen atom, a halogen atom, a hydroxy group, an alkoxy group, a nitro group, or an alkyl group, an aryl group, both of which may have a substituent(s), and n stands for an integer of 0 or 1.

Here, the photosensitive layer may comprise a layer including a dispersion of charge generating substance and a charge transporting substance selected from hydrazone compounds represented by the general formulae (II) in a binder resin.

A photoconductor as claimed in claim 4, wherein the photosensitive layer comprises a laminate of a charge transporting layer including a charge transporting substance selected from hydrazone compounds represented by the general formula (II) and a charge generating layer.

In the third aspect of the present invention, a photoconductor for electrophotography comprises:
a substrate; and
a photosensitive layer formed on the substrate and including at least one hydrazone compound represented by the following general formula (III) as a charge transporting substance:

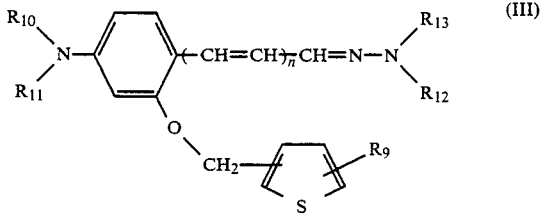

wherein, $R_{10}$, $R_{11}$, $R_{12}$ and $R_{13}$ stands for an alkyl group, an alkenyl group, an aryl group, an aralkyl group, each of which may have a substituent(s), at least one of $R_{10}$, $R_{11}$, $R_{12}$ and $R_{13}$ further stands for a thenyl group which may have a substituent(s), $R_9$ stands for a hydrogen atom, a halogen atom, a hydrony group, an alkoxy group, a nitro group, or an alkyl group, an aryl group, both of which may have a substituent(s), and n stands for an integer of 0 or 1.

Here, the photosensitive layer may comprise a layer including a dispersion of a charge generating substance and a charge transporting substance selected from hydrazone compounds represented by the general formula (III) in a binder resin.

The photosensitive layer may comprise a laminate of a charge transporting layer including a charge transporting substance selected from hydrazone derivatives compounds by the general formula (III) and a charge generating layer.

BRIEF DESCRIPTION OF THE DRAWINGS

FIGS. 1 to 3 are schematic cross-sectional views of photoconductors according to the present invention, respectively.

DETAILED DESCRIPTION OF PREFERRED EMBODIMENTS

The photoconductor according to the present invention which contains a hydrazone compound in the photosensitive layer thereof may be in the form of any one of the structures of FIGS. 1, 2 and 3, depending on the way of application of the hydrazone compound thereto.

FIGS. 1, 2 and 3 are schematic cross-sectional views of different embodiments of the photoconductor of the present invention, respectively.

FIG. 1 shows a monolayer type photoconductor. A photosensitive layer 2A is provided on an electroconductive substrate 1. The photosensitive layer 2A comprises a charge generating substance 3 and a hydrazone compound as a charge transporting substance 5 both of which substances are dispersed in a resin binder matrix so that the photosensitive layer 2A functions as photoconductor.

FIG. 2 shows a laminate type photoconductor. A laminated photosensitive layer 2B is provided on an electroconductive substrate 1, a lower layer of the laminate is a charge generating layer 4 including a charge generating substance 3 as the main component and an upper one is a charge transporting layer 6 containing a hydrazone compound as a charge transporting substance 5, so that the photosensitive layer 2B functions as a photoconductor. This photoconductor is usually used according to the negative charge mode.

FIG. 3 shows another laminate type photoconductor having a layer structure in reverse to that of FIG. 2. A laminated photosensitive layer 2C is provided on an electroconductive substrate 1, a lower layer of the laminate is a charge transporting layer 6 including a hydrazone compound as a charge transporting substance 5 and an upper one is a charge generating layer 4 including a charge generating substance 3. The photosensitive layer also functions as a photoconductor. This photoconductor is usually used according to the positive charge mode. In this case, a covering layer 7 may generally be further provided as shown in FIG. 3 to protect the charge generating layer 4.

Thus, there are two different types of layer structures in the photoconductor. The reason for this is that, even if any photoconductor with the layer structure as shown in FIG. 2 is to be used in the positive charge mode, no charge transporting substances adaptable to the positive charge mode have been found yet. Accordingly, when the positive charge mode is adapted, the photoconductor is required of a layer structure as shown in FIG. 3 at present.

A photoconductor as shown in FIG. 1 can be produced by dispersing a charge generating substance in a solution or a charge transporting substance and a resin binder and applying the resulting dispersion on an electroconductive substrate.

A photoconductor as shown in FIG. 2 can be prepared by depositing a charge generating substance on an electroconductive substrate by means of vacuum evaporation or applying and drying a dispersion of a particulate charge generating substance in a solvent and/or a resin binder on an electroconductive substrate, followed by applying a solution of a charge transporting substance and a resin binder on the resulting layer and drying.

A photoconductor as shown in FIG. 3 can be prepared by applying and drying a solution of a charge transporting substance and a resin binder on an electroconductive substrate, and depositing a charge generating substance on the resulting coating layer by means of vacuum evaporation or coating and drying a dispersion of a particulate charge generating substance in a solvent and/or a resin binder on the coating layer, followed by formation of a covering layer.

The electroconductive substrate 1 serves as an electrode of the photoconductor and as a support for a layer(s) formed thereon. The electroconductive substrate may be in the form of a cylinder, a plate or a film, and may be made of a metallic material such as aluminum, stainless steel or nickel, or other material having a surface treated to be electroconductive, such as glass so treated or a resin so treated.

The charge generating layer 4 is formed by application of a dispersion of a particulate charge generating substance 3 in a resin binder or by deposition of a charge generating substance by means of vacuum evaporation, or the like technique as described above, and this layer generates an electric charge upon receiving light. It is important that the charge generating layer 4 be high not only in charge generating efficiency but also in capability of injecting the generated electric charge into the charge transporting layer 6 and any covering layer 7, whose capability is desirably as little dependent upon the electric field as possible and high even in low intensity electric fields. Usable charge generating substances include phthalocyanine compounds such as metal-free phthalocyanine and titanyl phthalocyanine; various azo, quinone and indigo pigments; dyes such as cyanine, squarylium, azulenium, and pyrylium compounds; and selenium and selenium compounds. Among them, a suitable compound can be chosen depending on the wavelength range of a light source used for the image formation. The thickness of the charge generating layer is determined depending on the extinction coefficient of a charge generating substance to be used therein in view of the layer's function of generating an electric charge, but is generally 5 μm or smaller, preferably 1 μm or smaller. It also is possible to form a charge generating layer using a charge generating substance as a main component in mixture with a charge transporting substance and so on. Resin binders usable in the charge generating layer include polycarbonates, polyesters, polyamides, polyurethanes, epoxy resins, silicone resins, and methacrylate homopolymer and copolymers, which may be used either alone or in an appropriate composition ratio.

The charge transporting layer 6 is a coating film containing a hydrazone compound as an organic charge transporting substance in a resin binder. The charge transporting layer serves as an insulator layer in the dark so as to retain the electric charge of the photoconductor, and fulfills a function of transporting an electric charge injected from the charge generating layer upon receiving light. Resin binders usable in the charge transporting layer include polycarbonates, polyesters, polyamides, polyurethanes, epoxy resins, silicone resins, and methacryate homopolymer and copolymers.

The covering layer 7 has a function of receiving and retaining an electric charge generated by corona discharge in the dark and a capability of transmitting light to which the charge generating layer should respond. It is necessary that the covering layer transmits light upon exposure of the photoconductor and allows the light to reach the charge generating layer, and then undergoes the injection of an electric charge generated in the charge generating layer to neutralize and erases a surface electric charge. Materials usable in the covering layer include organic insulating film-forming materials such as polyesters and polyamides. Such organic materials may also be used in mixture with an inorganic material such as a glass resin or $SiO_2$, or a material for lowering electric resistance such as a metal or a metallic oxide. Materials usable in the covering layer are not limited to organic insulating materials for film-forming, and further include inorganic materials such as $SiO_2$, metals, and metallic oxides, which may be formed into a covering layer by an appropriate method such as vacuum evaporation and deposition, or sputtering. From the viewpoint of the aforementioned description, it is desirable that the material to be used in the covering layer be as transparent as possible in the wavelength range in which the charge generating substance attains maximum light absorption.

Although the thickness of the covering layer depends on the material or composition thereof, it can be arbitrarily set in so far as it does not produce any adverse effects including an increase in a residual potential in continuous repeated use.

The hydrazone compounds to be used in the present invention include three groups of compounds, each of which can be easily synthesized by a customary method.

The first group of hydrazone compounds is represented by the following general formula (I).

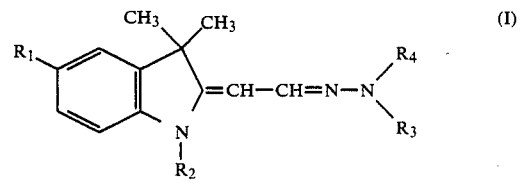

Wherein, $R_1$ stands for a hydrogen atom, a halogen atom, a hydroxy group, an alkoxy group, or a nitro group, each of $R_2$, $R_3$ and $R_4$ stands for an aryl group, an alkyl group, an aralkyl group or an alkenyl group, each of which may have a substituent(s), and at least one of $R_2$, $R_3$ and $R_4$ stands for a thenyl group which may have a substituent(s).

These compounds are synthesized by dehydration-condensating an aldehyde compound of the formula

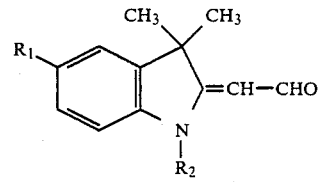

with a hydrazine compound of the formula

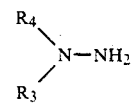

in an appropriate organic solvent such as ethanol in the presence of a small amount of a catalyst such as an acid.
Specific examples of the hydrazone compounds of the general formula (I) prepared in the above-mentioned manner include:
COMPOUND
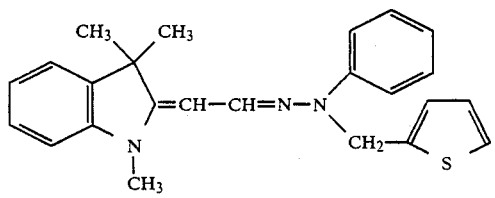
No. I-1
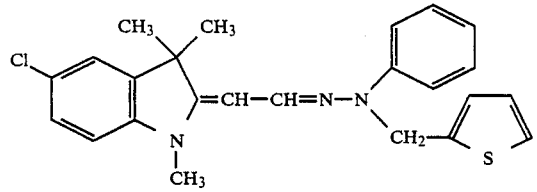
No. I-2
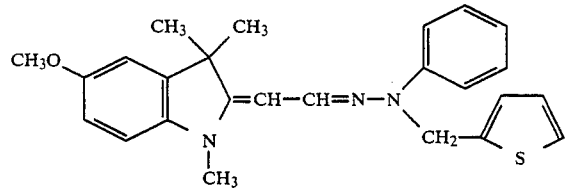
No. I-3
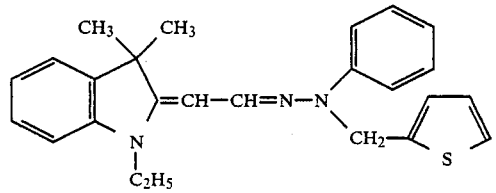
No. I-4
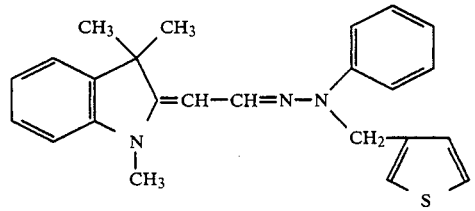
No. I-5
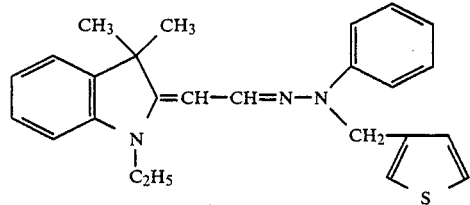
No. I-6
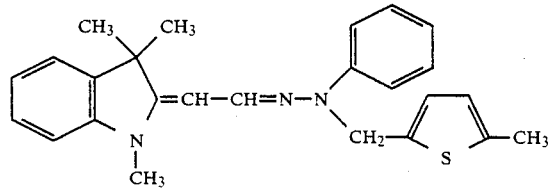
No. I-7

| COMPOUND | |
|---|---|
| 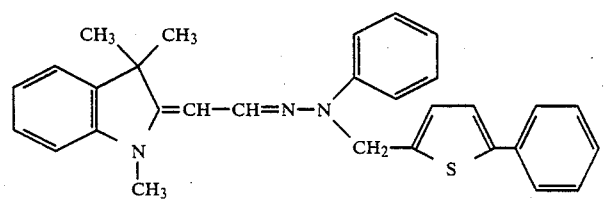 | No. I-8 |
| 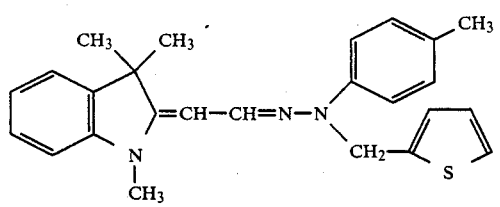 | No. I-9 |
| 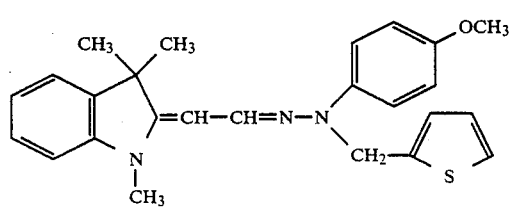 | No. I-10 |
| 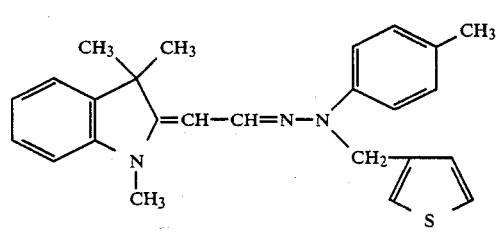 | No. I-11 |
| 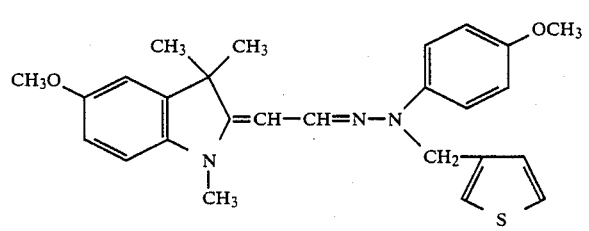 | No. I-12 |
| 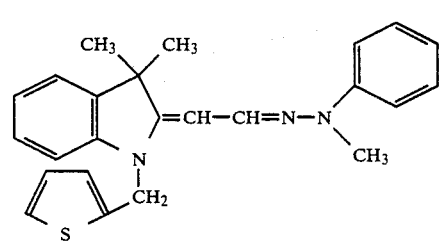 | No I-13 |
| 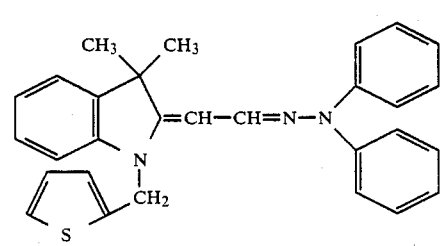 | No I-14 |

COMPOUND
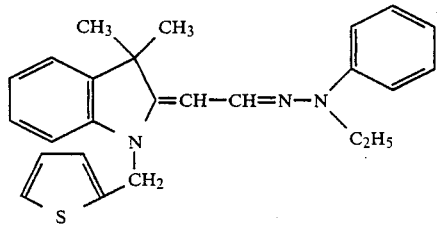 No I-15
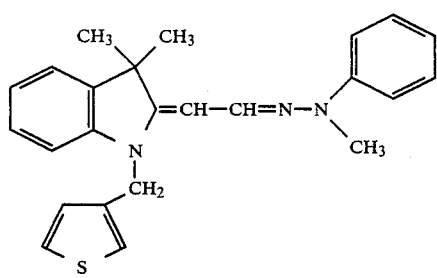 No I-16
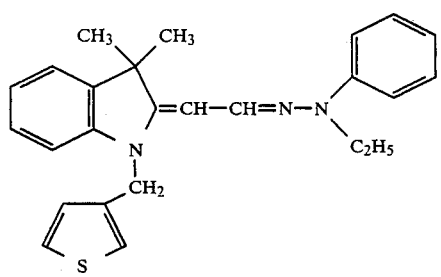 No I-17
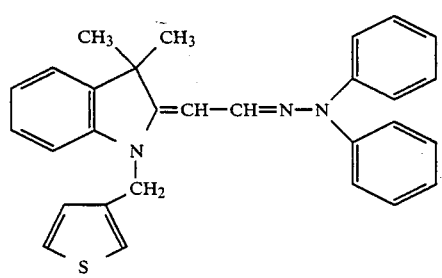 No I-18
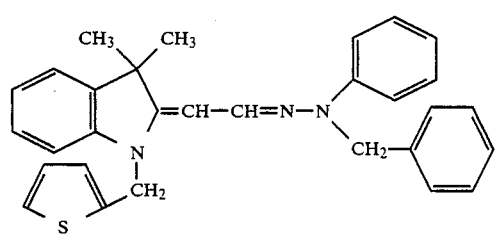 No I-19
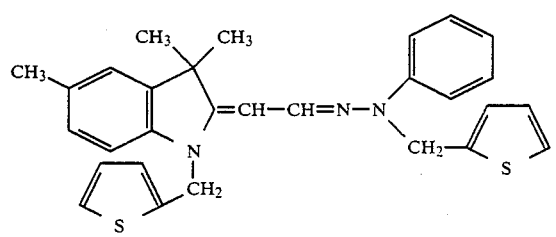 No I-20

COMPOUND

No I-21
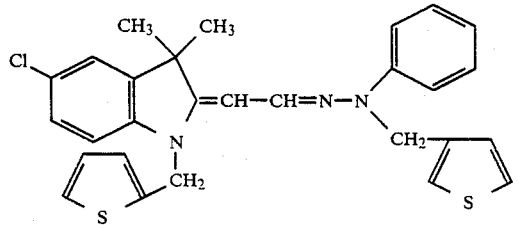

No I-22
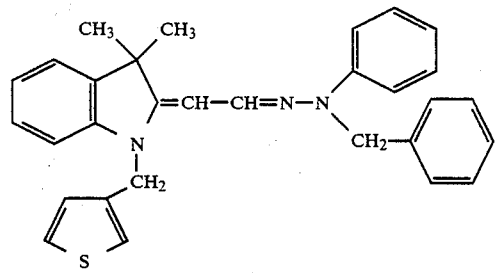

No I-23
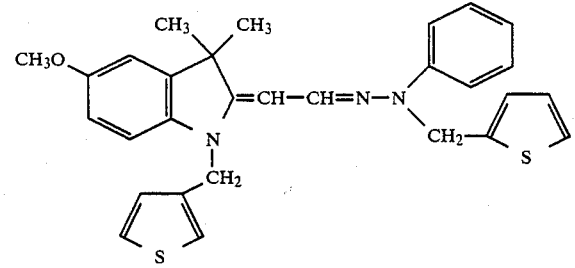

No I-24
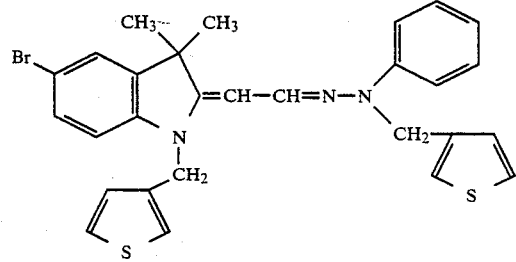

The second group of hydrazone compounds is represented by the following general formula (II).

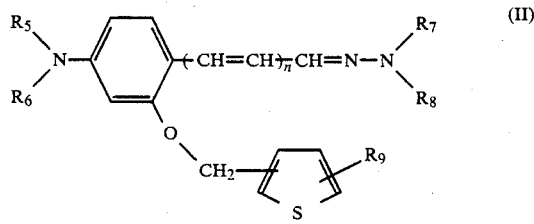

Wherein, $R_5$, $R_6$, $R_7$ and $R_8$ stands for an alkyl group, an alkenyl group, an aryl group, or an aralkyl group, each of which may have a substituent(s), $R_9$ stands for a hydrogen atom, a halogen atom, a hydroxy group, an alkoxy group, or an alkyl group, an aryl group, both of which may have a substituent(s), and n stands for an integer of 0 or 1.

These compounds are synthesized by dehydration-condensating an aldehyde compound of the formula

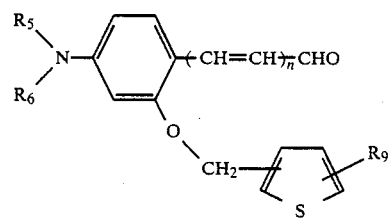

with a hydrazine compound of the formula

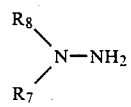

in an appropriate organic solvent such as ethanol in the presence of a small amount of a catalyst such as an acid.
Specific examples of the hydrazone compounds of the general formula (II) prepared in the above-mentioned manner include:
COMPOUND
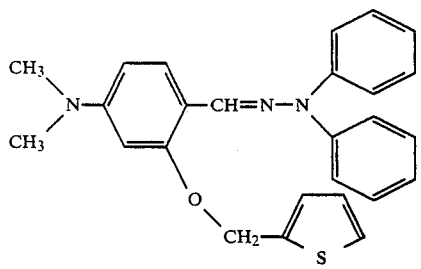
No II-1
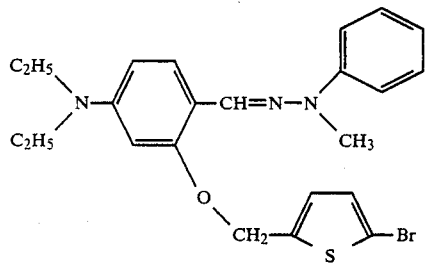
No II-2
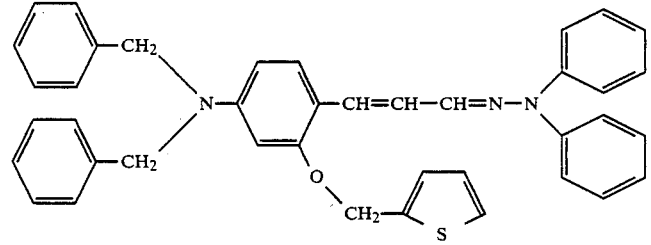
No II-3
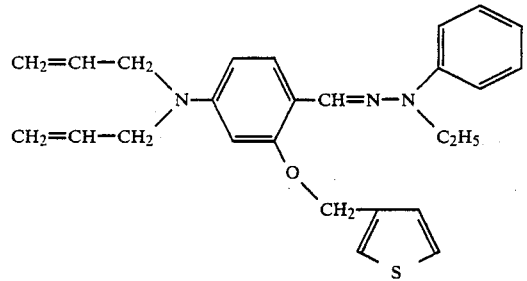
No II-4
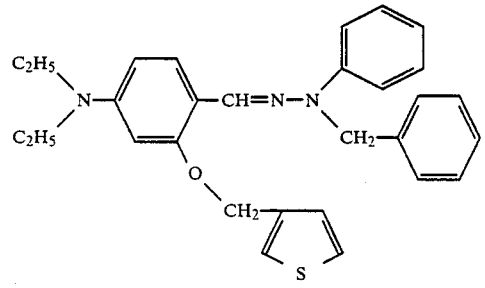
No II-5

-continued
COMPOUND
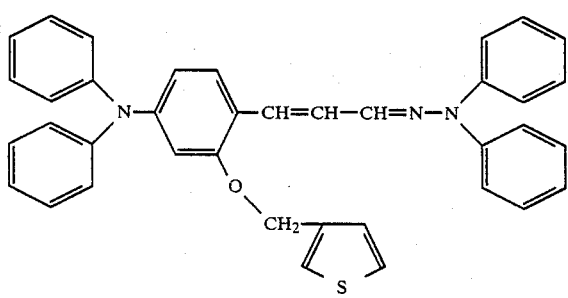
No II-6
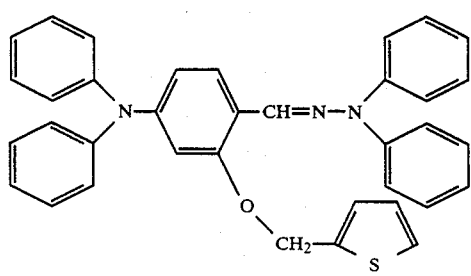
No II-7
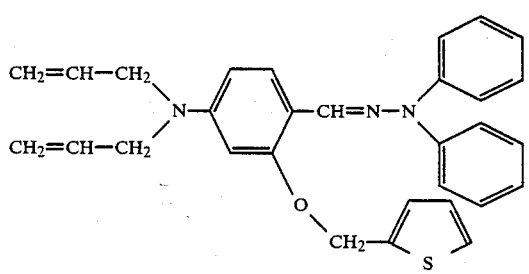
No II-8
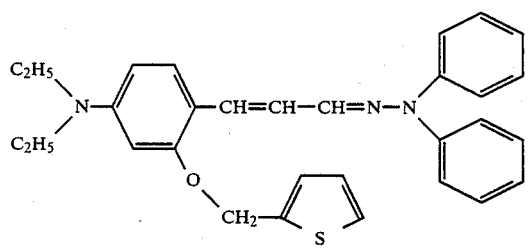
No II-9
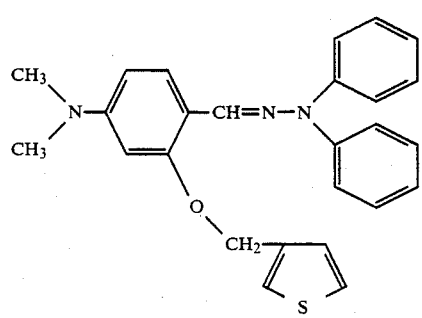
No II-10

COMPOUND

No II-11

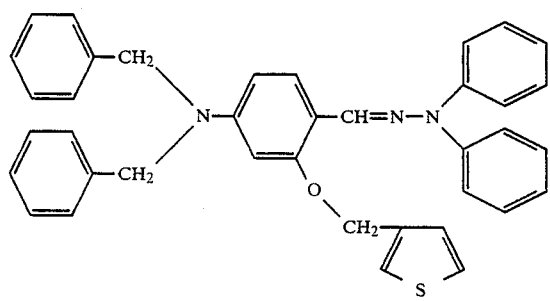

No II-12

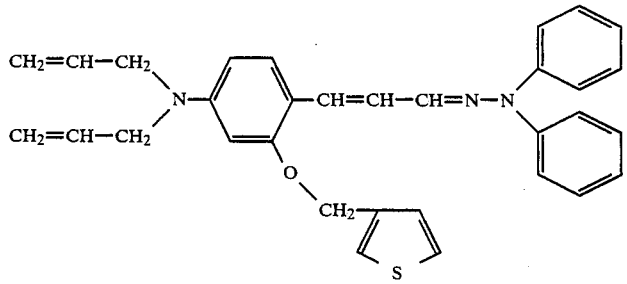

The third group of hydrazone compounds is represented by the following general formula (III).

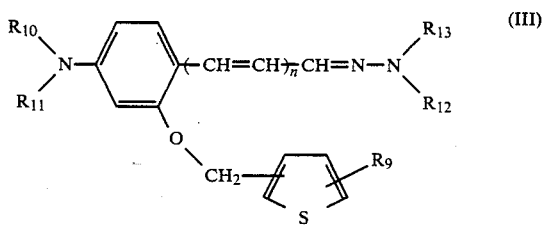

Wherein, $R_9$ is the same as in the general formula (II), each of $R_{10}$, $R_{11}$, $R_{12}$ and $R_{13}$ stands for an alkyl group, analkenyl group, an aryl group, or an aralkyl group, each of which may have a substituent(s), at least one of $R_{10}$, $R_{11}$, $R_{12}$ and $R_{13}$ further stands for a thenyl group which may have a substituent(s).

The compounds represented by the general formula (III) can be synthesized :n the same manner as :n the case of the compounds represented by the general formula (II).

Specific examples of the hydrazone compounds of the general formula (III) prepared in the above-mentioned manner include:

COMPOUND

No III-1

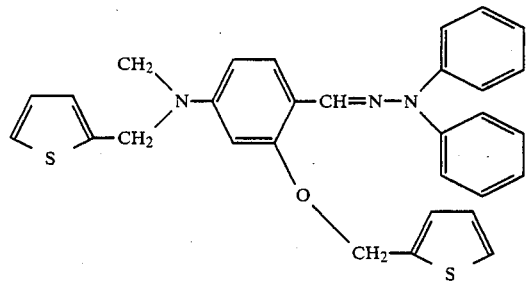

No III-2

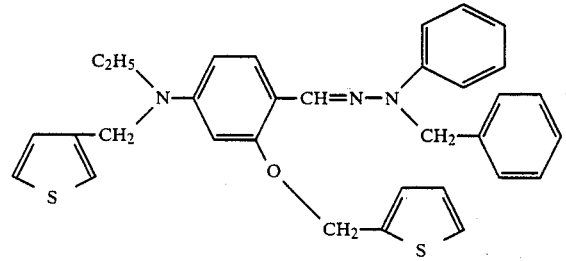

-continued
| COMPOUND |
|---|
| No III-3 |
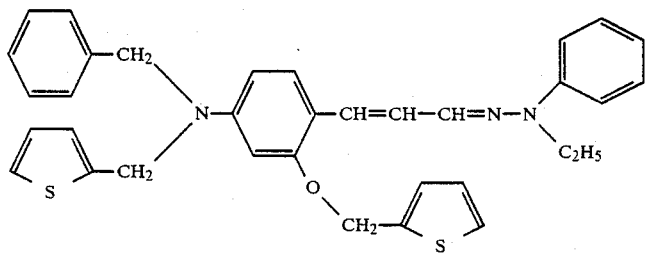
No III-4
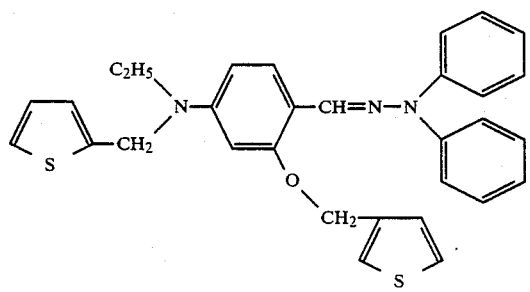
No III-5
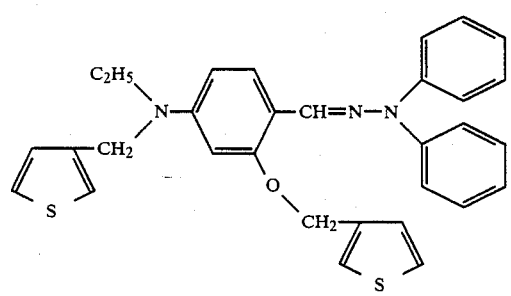
No III-6
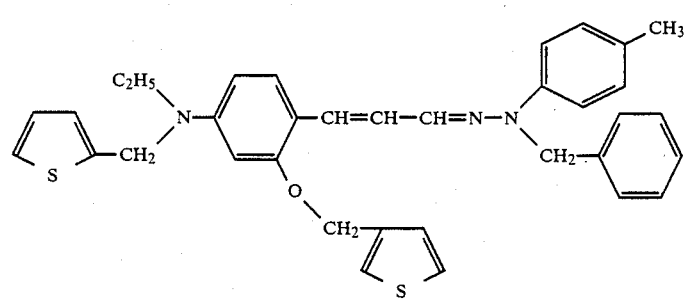
No III-7
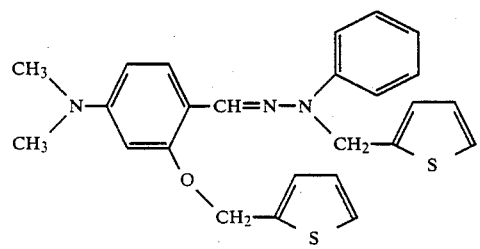

-continued
| | COMPOUND |
|---|---|
| 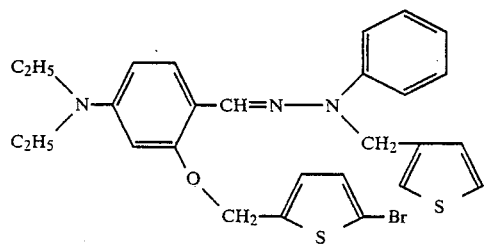 | No III-8 |
| 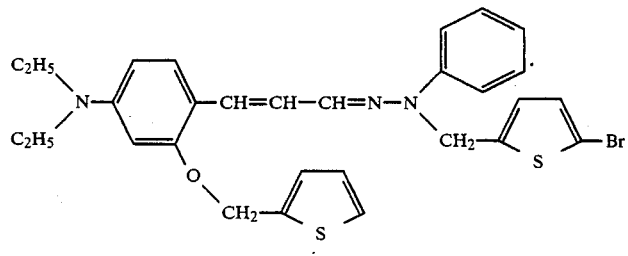 | No III-9 |
| 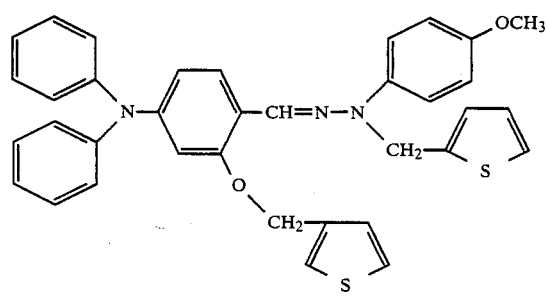 | No III-10 |
| 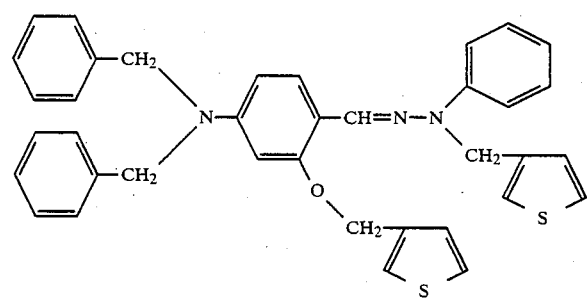 | No III-11 |
| 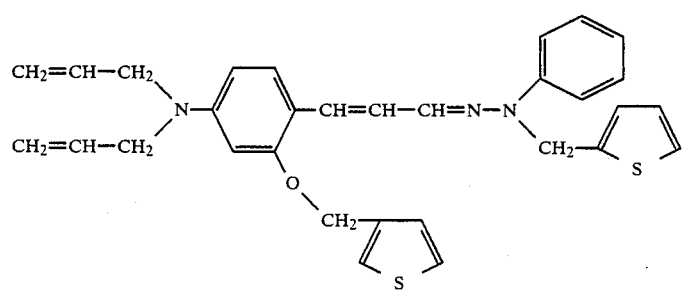 | No III-12 |

| | COMPOUND |
|---|---|
| 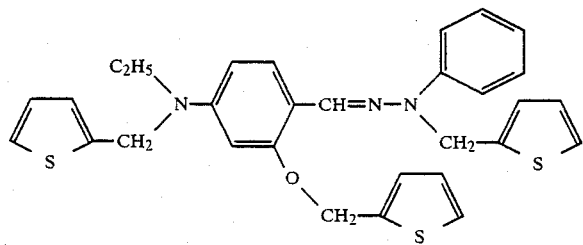 | No III-13 |
| 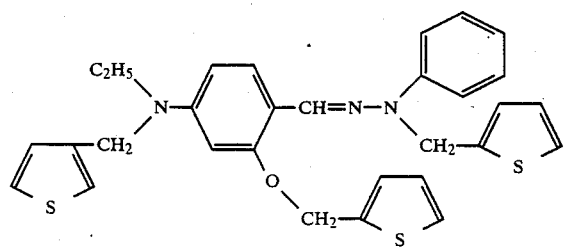 | No III-14 |
| 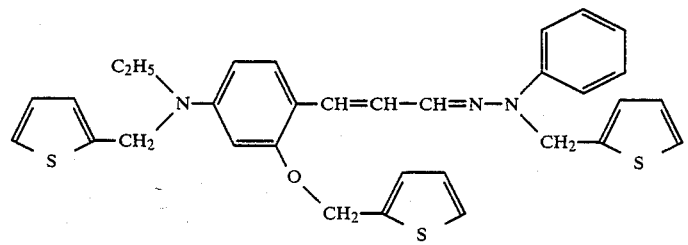 | No III-15 |
| 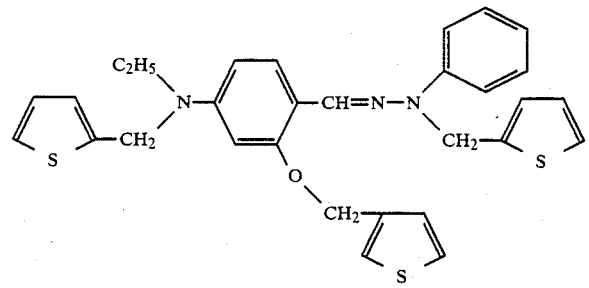 | No III-16 |
| 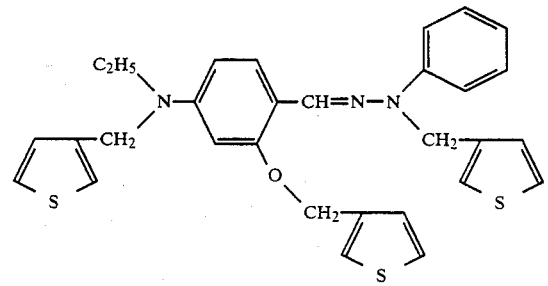 | No III-17 |

COMPOUND
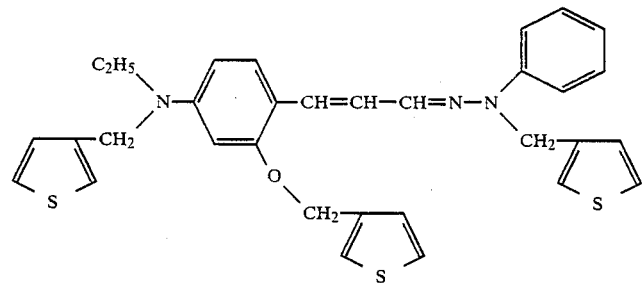
No III-18
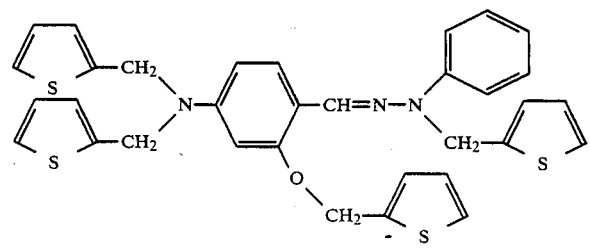
No III-19
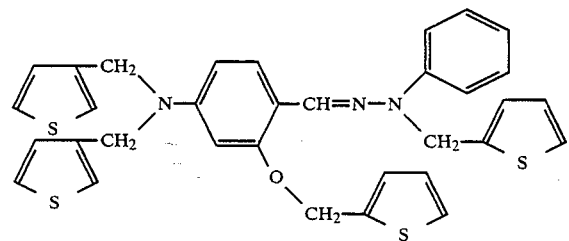
No III-20
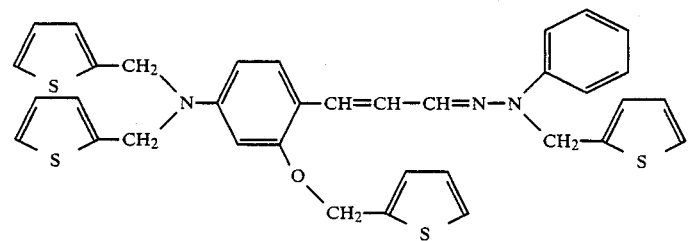
No III-21
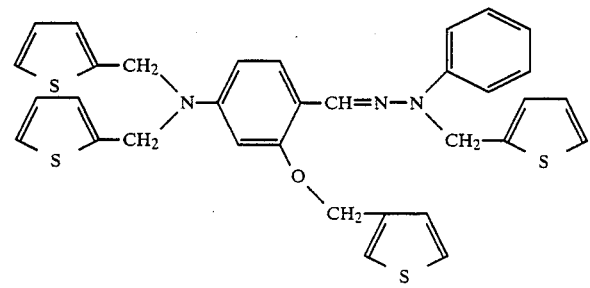
No III-22

-continued

COMPOUND

No III-23

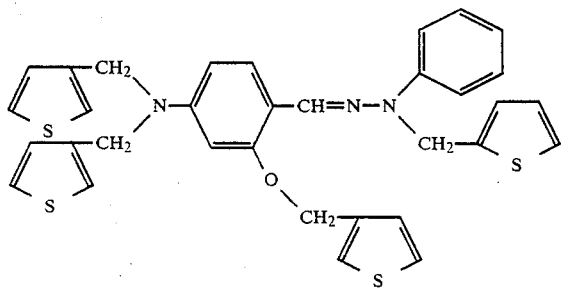

No III-24

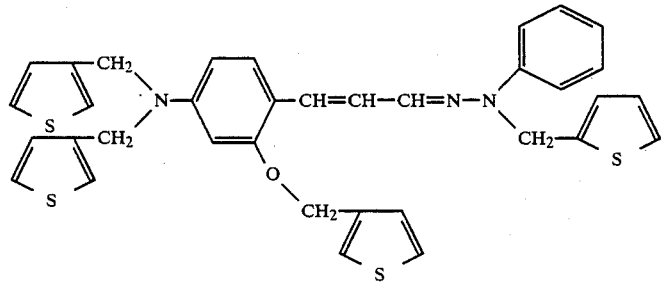

Example will now be given, wherein various compounds represented by the general formula (I) were respectively used to produce photoconductos.

EXAMPLE 1

50 parts by weight of metal-free phthalocyanine (manufactured by Tokyo Kasei Co., Ltd.) pulverized with a ball mill for 150 hours and 100 parts by weight of the hydrazone compound No. I-1 mentioned above were kneaded together with 100 parts by weight of a polyester resin (Vylon 200 (trademark), manufactured by Toyobo Co., Ltd.) and tetrahydrofuran (THF) as a solvent with a mixer for 3 hours to prepare a coating liquid. The coating liquid was applied on an aluminum-deposited polyester film (Al-PET) as an electroconductive substrate by means of the wire bar technique to form a photosensitive layer having a dry thickness of 15 μm. Thus, a photoconductor with the structure shown in FIG. 1 was produced.

EXAMPLES 2 and 3

The photoconductors of Examples 2 and 3 were produced in substantially the same manner as in Example 1 except that the compounds No. II-1 and No. III-1 were used instead of the hydrazone compound No. I-1 in Example 1.

EXAMPLE 4

Metal-free α-phthalocyanine as a starting material was pulverized for 20 minutes into a fine powder with a pulverizer, a LIMMAC (Linear Induction Motor Mixing and Crushing manufactured by Fuji Electric Co., Ltd.) wherein a non-magnetic can containing the metal-free α-phthalocyanine and Teflon pieces as small acting pieces was placed between two linear motors faced each other. The sample of 1 part by weight of the fine powder thus prepared was dispersed in 50 parts by weight of DMF (N, N-dimethylformamide) as a solvent by means of an ultrasonic dispersion treatment. Thereafter, the sample was separated from DMF by filtration and dried to complete the treatment of metal-free phthalocyanine.

A solution of 100 parts by weight of the hydrazone compound No. I-2 mentioned above in 700 parts by weight of tetrahydrofuran (THF) was mixed with a solution of 100 parts by weight of polymethyl methacrylate (PMMA, manufactured by Tokyo Kasei Co., Ltd.) in 700 parts by weight of toluene to prepare a coating liquid. The coating liquid was applied on an aluminum-deposited polyester film substrate by means of the wire bar technique to form a charge transporting layer having a dry thickness of 15 μm. 50 parts by weight of metal-free phthalocyanine treated in the above-mentioned manner, and 50 parts by weight of a polyester resin (Vylon 200), were kneaded with a mixer for 3 hours together with THF as a solvent to prepare a coating liquid, which was then applied on the charge transporting layer by the wire bar technique to form a charge generating layer having a dry thickness of 1 μm. Thus, a photoconductor with a structure corresponding to that shown in FIG. 3 was produced. A covering layer, which was not directly related to the present invention, was not provided.

EXAMPLES 5 AND 6

The photoconductors of Examples 5 and 6 were produced in substantially the same manner as in Example 1 except that the compounds No. II-2 and No. III-2 were used instead of the hydrazone compound No. I-2 in Example 4.

EXAMPLE 7

A photoconductor was produced by forming a photosensitive layer in substantially the same manner as in Example 1 except that 50 parts by weight of metal-free phthalocyanine, 100 parts by weight of the hydrazone compound No. I-3 mentioned above, 50 parts by weight of a polyester resin (nylon 200), and 50 parts by weight of PMMA were used to replace therewith the composition of the photosensitive layer of Example 1.

EXAMPLES 8 AND 9

The photoconductors of Examples 8 and 9 were produced in substantially the same manner as in Example 7 except that the compounds No. II-3 and No. III-3 were used instead of the hydrazone compound No. I-3 in Example 7.

EXAMPLE 10

A photoconductor was produced by forming a photosensitive layer in substantially the same manner as in Example 4 except that Chlorodiane Blue which is a bisazo pigment disclosed in, for example, Japanese Patent Laid-Open No. 37,543/1972 was used instead of metal-free phthalocyanine in the Example 4.

EXAMPLES 11 AND 12

The photoconductors of Examples 11 and 12 were produced in substantially the same manner as in Example 10 except that the compounds No. II-2 and No. III-2 were used instead of the hydrazone compound No. I-2 in Example 10.

The electrophotographic characteristics of the twelve photoconductors thus produced were measured by utilizing an electrostatic recording paper testing apparatus (Kawaguchi Denki Model SP-428).

The surface potential $V_s$ (volts) of each photoconductor is an initial surface potential which was measured when the surface of the photoconductor was positively charged in the dark by corona discharge at 6.0 kV for 10 seconds. After the discontinuation of the corona discharge, the photoconductor was allowed to stand in the dark for 2 seconds, after which the surface potential $V_d$ (volts) of the photoconductor was measured. Subsequently, the surface of the photoconductor was irradiated with white light at an illuminance of 2 luxes and the time (seconds) required for the irradiation to decrease the surface potential of the photoconductor to half of the $V_d$ was measured, then from which time and the illuminance the half decay exposure amount $E_{\frac{1}{2}}$ (lux.sec) was calculated. Also, the surface potential of the photoconductor after 10 seconds of irradiation thereof with white light at an illuminance of 2 luxes was measured as a residual potential $V_r$ (volts). When a phthalocyanine compound was used as a charge generating substance, a high sensitivity could be expected for light with longer wavelengths. Hence, the electrophotographic characteristics thereof were also measured by using a monochromatic light with a wavelength of 780 nm. Specifically, the $V_s$ and the $V_d$ of each photoconductor were measured in the same manner as described above, and the half decay exposure amount ($\mu J/cm^2$) was found by irradiation of the photoconductor surface with a monochromatic light (wavelength: 780 nm) of 1 $\mu W$ instead of white light, while the residual potential $V_r$ (volts) was measured after 10 seconds of irradiation of the photoconductor surface with the above-mentioned light. The results of the measurements are shown in Table 1.

TABLE 1

| Example No. | White Light | | | Light with Wavelength of 780 nm | | |
|---|---|---|---|---|---|---|
| | $V_s$ (volts) | $V_r$ (volts) | $E_{\frac{1}{2}}$ (lux·sec) | $V_r$ (volts) | $V_r$ (volts) | $E_{\frac{1}{2}}$ ($\mu J/cm^2$) |
| 1 | 630 | 70 | 6.8 | 630 | 80 | 7.3 |
| 2 | 600 | 80 | 7.7 | 660 | 90 | 7.0 |
| 3 | 550 | 100 | 7.2 | 560 | 100 | 6.8 |
| 4 | 600 | 60 | 6.1 | 620 | 100 | 6.5 |
| 5 | 650 | 100 | 6.8 | 630 | 110 | 6.1 |
| 6 | 630 | 80 | 5.8 | 600 | 60 | 6.2 |
| 7 | 580 | 90 | 5.4 | 630 | 70 | 6.1 |
| 8 | 660 | 90 | 6.0 | 620 | 80 | 6.5 |
| 9 | 650 | 70 | 6.4 | 630 | 80 | 5.9 |
| 10 | 630 | 100 | 6.9 | — | — | — |
| 11 | 630 | 70 | 6.1 | — | — | — |
| 12 | 640 | 80 | 6.3 | — | — | — |

As can be seen in Table 1, the photoconductors of Examples 1 to 12 were not substantially different therebetween in the half decay exposure amounts and the residual potentials, and showed good surface potential characteristics. The photoconductors of Examples 1 to 9, using a phthalocyanine compound as a charge generating substance, showed also excellent electrophotographic characteristics for light with a long wavelength of 780 nm.

EXAMPLE 13

Selenium was deposited on an aluminum plate having a thickness of 500 $\mu m$ by means of vacuum evaporation to form a charge generating layer having a thickness of 1.5 $\mu m$. A solution of 100 parts by weight of the hydrazone compound No. I-4 as mentioned above in 700 parts by weight of tetrahydrofuran (THF) was mixed with a solution of 100 parts by weight of polymethyl methacrylate (PMMA) in 700 parts by weight of toluene to prepare a coating liquid, which was then applied on the charge generating layer by the wire bar technique to form a charge transporting layer having a dry thickness of 20 $\mu m$. Thus, a photoconductor with the structure shown in FIG. 2 was produced. This photoconductor was charged by corona discharge at $-6.0$ kV for 0.2 second and examined with respect to electrophotographic characteristics to obtain good results, namely $V_s = -650$ V, $V_r = -50$ V and $E_{\frac{1}{2}} = 6.0$ lux.sec.

EXAMPLES 14 AND 15

The photoconductors of Examples 15 and 16 were produced in substantially the same manner as in Example 13 except that the compounds No. II-4 and No. III-4 were used instead of the hydrazone compound No. I-4 in Example 13. When the electrophotographic characteristics of these examples were measured in the same manner as in Example 13, good results were obtained, namely, $V_s = -$ V, $V_r = -40$ V, and $E_{\frac{1}{2}} = 5.3$ lux.sec. for Example 14, and $V_s = -600$ V, $V_r = -50$ V and $E_{\frac{1}{2}} = 4.9$ lux.sec. for Example 15.

EXAMPLE 16

50 parts by weight of metal-free phthalocyanine treated in the same manner as in Example 4, 50 parts by weight of a polyester resin (Vylon 200), and 50 parts by weight of PMMA were kneaded together with THF as a solvent with a mixer for 3 hours to prepare a coating liquid, which was then applied on an aluminum support to form a charge generating layer having a thickness of about 1 $\mu m$. Subsequently, 100 parts by weight of the hydrazone compound No. I-5 as mentioned above, 100 parts by weight of a polycarbonate resin (Panlite L-

1250, manufactured by Teijin Kasei Co., Ltd.), and 0.1 part by weight of a silicone oil were mixed with 700 parts by weight of THF and 700 parts by weight of toluene to prepare a coating liquid, which was then applied on the charge generating layer to form a charge transporting layer having a thickness of about 15 μm.

The photoconductor thus produced was charged by corona discharge at −6.0 kV for 0.2 second and examined with respect to electrophotographic characteristics in the same manner as in Example 13 to obtain good results, namely $V_s = -650$ V and $E_{\frac{1}{2}} = 4.9$ lux.sec.

EXAMPLES 17 and 18

The photoconductors of Examples 17 and 18 were produced in substantially the same manner as in Example 16 except that the compounds No. II-5 and No. III-5 were used instead of the hydrazone compound No. I-5 in Example 16. When the electrophotographic characteristics of these photoconductors were measured in the same manner as in Example 13, good results were obtained, namely $V_s = -620$ V, $E_{\frac{1}{2}} = 5.1$ lux.sec. for Example 17 and $V_s = -650$ V $E_{\frac{1}{2}} = 6.4$ lux.sec. for Example 18.

EXAMPLE 19

Photoconductors were produced in substantially the same manner as in Example 10 except the that the hydrazone compounds Nos. I-6 to I-24, Nos. II-6 to II-12 and Nos. III-6 to III-24 were respectively used instead of the compound No. I-2. The results obtained by using the electrostatic recording paper testing apparatus (SP-428) are shown in Table 2. Table 2 shows the half decay exposure amounts $E_{\frac{1}{2}}$(lux.sec) obtained under the experimental conditions where the photoconductors were positively charged in the dark by corona discharge at +6.0 kV for 10 seconds and irradiated with white light at an illuminance of 2 luxes.

TABLE 2

| Compound No. | $E_{\frac{1}{2}}$ (lux · sec.) |
|---|---|
| I-6 | 6.6 |
| I-7 | 6.6 |
| I-8 | 8.0 |
| I-9 | 7.3 |
| I-10 | 7.9 |
| I-11 | 8.2 |
| I-12 | 7.9 |
| I-13 | 7.6 |
| I-14 | 6.6 |
| I-15 | 6.2 |
| I-16 | 6.4 |
| I-17 | 6.8 |
| I-18 | 7.1 |
| I-19 | 7.3 |
| I-20 | 6.5 |
| I-21 | 5.5 |
| I-22 | 5.9 |
| I-23 | 6.7 |
| I-24 | 6.4 |
| II-6 | 6.7 |
| II-7 | 6.8 |
| II-8 | 6.4 |
| II-9 | 6.8 |
| II-10 | 6.8 |
| II-11 | 6.7 |
| II-12 | 6.1 |
| III-6 | 7.1 |
| III-7 | 6.3 |
| III-8 | 7.6 |
| III-9 | 6.1 |
| III-10 | 5.8 |
| III-11 | 7.1 |
| III-12 | 6.9 |
| III-13 | 6.8 |
| III-14 | 6.2 |
| III-15 | 7.8 |
| III-16 | 7.2 |
| III-17 | 7.3 |
| III-18 | 5.8 |
| III-19 | 6.6 |
| III-20 | 5.8 |
| III-21 | 6.4 |
| III-22 | 7.1 |
| III-23 | 7.6 |
| III-24 | 6.5 |

As can be seen in Table 2, the photoconductors using the respective hydrazone compounds Nos. I-6 to I-24 Nos. II-6 to II-12 and Nos. III-6 to III-24 were satisfactory with respect to the half decay exposure amount $E_{178}$.

According to the present invention, since a hydrazone compound represented by any one of the aforementioned chemical formulae is used in a photosensitive layer formed on an electroconductive substrate, as a charge transporting substance, a photoconductor shows a high sensitivity and excellent characteristics in repeated use when adapted to either a positive charge mode or a negative charge mode. A suitable charge generating substance can be chosen so as to be adapted to the kind of exposure light source. By way of example, a phthalocyanine compound or a bisazo compound can be used as a charge generating substance to provide a photoconductor capable of being used in semiconductor laser printers. If necessary, a covering layer may be provided on the surface of a photoconductor to improve the durability thereof.

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:
1. A photoconductor for electrophotography, comprising:
an electroconductive substrate; and
a photosensitive layer formed on said electroconductive substrate and including a charge generating substance and a charge transporting substance comprising at least one hydrazone compound represented by general formula (I):

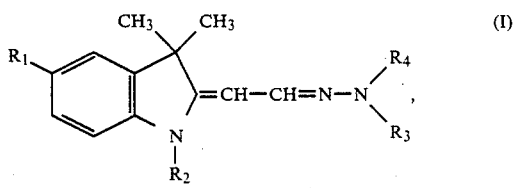

wherein R1 is selected from the group consisting of a hydrogen atom, a halogen atom, a hydroxy group, an alkoxy group , and a nitro group, each of R2, R3 and R4 is selected from the group consisting of an aryl group, an alkyl group, an aralkyl group, and an alkenyl group, each of which group may have a substituent(s), and at least one of R2, R3 and R4 is a thenyl group which may have a substituent(s).

2. A photoconductor as claimed in claim 1, wherein said photosensitive layer comprises a layer including a dispersion of a charge generating substance and a charge transporting substance selected from hydrazone compounds represented by the general formula (I) in a binder resin.

3. A photoconductor as claimed in claim 1, wherein said photosensitive layer comprises a laminate of a charge transporting layer including a charge transporting substance selected from hydrazone compounds represented by the general formula (I) and a charge generating layer.

4. A photoconductor for electrophotography, comprising:
an electroconductive substrate; and
a photosensitive layer formed on said electroconductive substrate and including a charge generating substance and a charge transporting substance comprising at least one hydrazone compound represented by general formula (II):

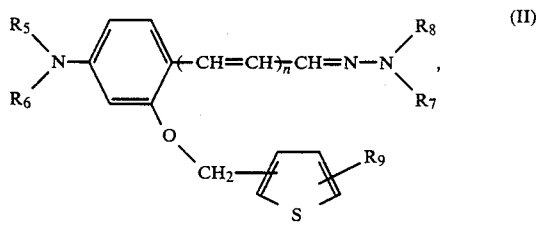

wherein each of R5, R6, R7 and R8 is selected from the group consisting of an alkyl group, an alkenyl group, an aryl group, and an aralkyl group, each of which group may have a substituent(s), R9 is selected from the group consisting of a hydrogen atom, a halogen atom, a hydroxy group, an alkoxy group, a nitro group, an alkyl group, and an aryl group, each of the last two groups of which may have a substituents(s) and n is an integer and has a value of 0 or 1.

5. A photoconductor as claimed in claim 4, wherein said photosensitive layer comprises a layer including a dispersion of charge generating substance and a charge transporting substance selected from hydrazone compounds represented by the general formulae (II) in a binder resin.

6. A photoconductor as claimed in claim 4, wherein said photosensitive layer comprises a laminate of a charge transporting layer including a charge transporting substance selected from hydrazone compounds represented by the general formula (II) and a charge generating layer.

7. A photoconductor for electrophotography, comprising:
an electroconductive substrate; and
a photosensitive layer formed on said electroconductive substrate and including a charge generating substance and a charge transporting substance comprising at least one hydrazone compound represented by general formula (III):

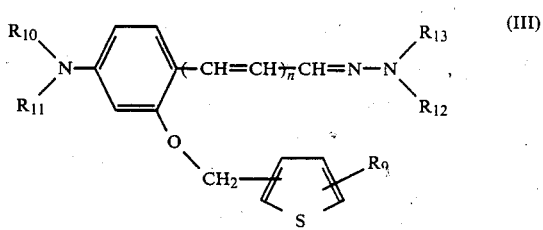

wherein each of R10, R11, R12 and R13 is selected from the group consisting of an alkyl group, an alkenyl group, an aryl group, and an aralkyl group, each of which group may have a substituent(s), and wherein at least one of R10, R11, R12 and R13 is a thenyl group which may have a substituent(s), R9 is selected from the group consisting of a hydrogen atom, a halogen atom, a hydroxy group, an alkoxy group, a nitro group, an alkyl group, and an aryl group, each of the last two groups of which may have a substituent(s), and n is an integer and has a value of 0 or 1.

8. A photoconductor as claimed in claim 7, wherein said photosensitive layer comprises a layer including a dispersion of a charge generating substance and a charge transporting substance selected from hydrazone compounds represented by the general formula (III) in a binder resin.

9. A photoconductor as claimed in claim 7, wherein said photosensitive layer comprises a laminate of a charge transporting layer including a charge transporting substance selected from hydrazone derivatives compounds by the general formula (III) and a charge generating layer.

* * * * *